United States Patent [19]

Gunderson

[11] 4,196,725
[45] Apr. 8, 1980

[54] CARDIAC PULMONARY RESUSCITATION APPARATUS

[75] Inventor: Arthur M. Gunderson, St. Cloud, Minn.

[73] Assignee: RescueTech Corporation, St. Cloud, Minn.

[21] Appl. No.: 895,733

[22] Filed: Apr. 13, 1978

[51] Int. Cl.² .......................................... A61H 31/00
[52] U.S. Cl. ............................................... 128/205.25
[58] Field of Search .............................. 128/28, 145.8

[56] References Cited

U.S. PATENT DOCUMENTS

| | | | |
|---|---|---|---|
| 3,351,052 | 11/1967 | Hewson | 128/145.8 |
| 3,414,896 | 12/1968 | Glick et al. | 128/145.8 |
| 3,461,858 | 8/1969 | Michelson | 128/28 |
| 3,613,677 | 10/1971 | Blasko | 128/145.8 |
| 4,106,502 | 8/1978 | Wilson | 128/145.8 |

Primary Examiner—William E. Kamm

[57] ABSTRACT

A Cardiac Pulmonary Resuscitation Apparatus consisting of a carrier carton containing basic emergency life support elements comprising a rigid spine board, a pull-out operating panel having mounted thereon a device for positioning the head of a subject to open an air flow passage, a pump, an air hose from the pump to a respiratory face mask, an oxygen line from an oxygen tank disposed in the carton to the air hose and a rhythm device carried by the panel, the respiratory face mask and the head positioning device cooperating to have the mask in a sealed operating position over the mouth and nose of the subject secured by straps carried by the head positioning device, the mask including a valve passing oxygen enriched air under pump pressure and in the alternative passing ambient air under atmospheric pressure to the subject and an indicating relief valve in connection with the air under pressure.

2 Claims, 4 Drawing Figures

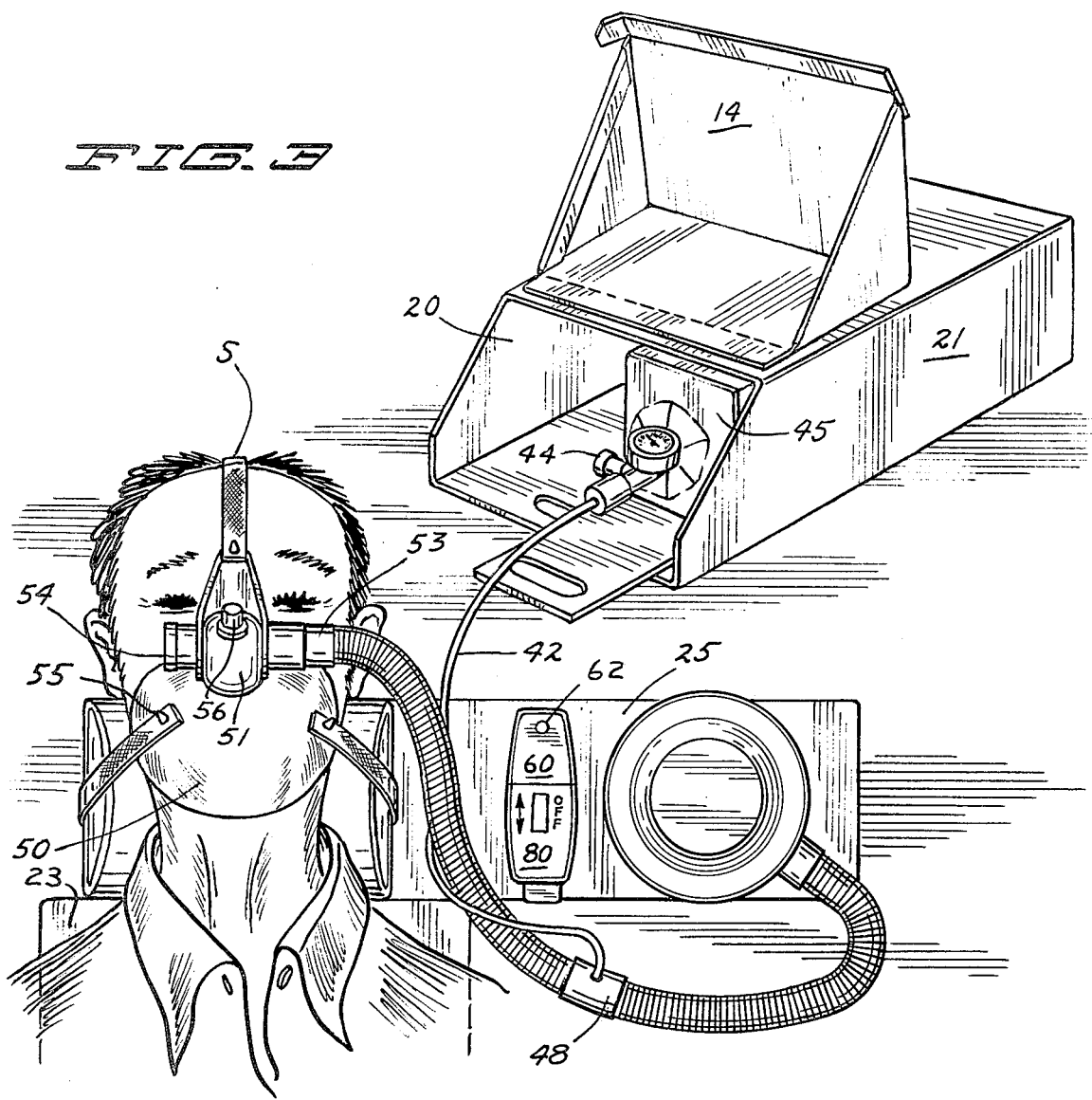
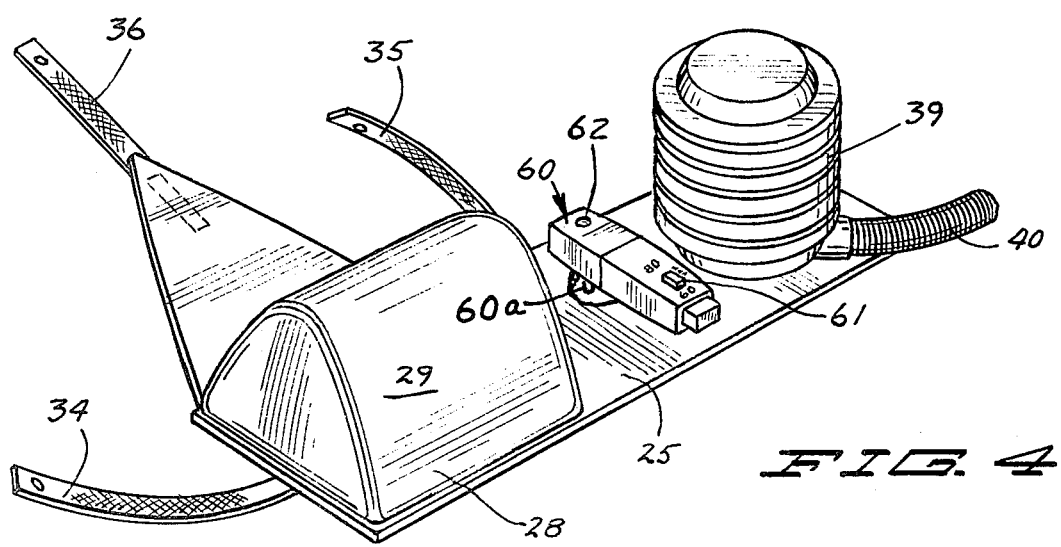

CARDIAC PULMONARY RESUSCITATION APPARATUS

BACKGROUND OF THE INVENTION

1. Field of the Invention.

This invention relates to an apparatus in connection with applying respiratory assistance and external chest compression for cardiac pulmonary resuscitation.

2. Description of the Prior Art.

Prior art structure to the extent known embody oxygen cylinders and face masks for the application of oxygen but are not known to provide an operative arrangement of a face mask embodying a valve and a pressure relief valve for the application of oxygen enriched air or in the alternative ambient air in respiratory assistance and a device for positioning the head of the subject to open his air passage and a like operational arrangement of the component parts in connection therewith to assist in external cardiac compression.

SUMMARY OF THE INVENTION

This invention relates to an apparatus for respiratory assistance or restoration and for cardiac pulmonary resuscitation.

It is an object of this invention to provide an apparatus comprising an operating arrangement of elements necessary to position the head of a subject to open an air flow passage, to provide an oxygen enriched air supply to assist in the effort to restore respiration in the case of respiratory arrest and to provide a rhythm element to time external cardiac compression in the effort to restore heart action in the case of a cardiac arrest.

It is more particularly an object of this invention to provide an apparatus combining in operative relationship a panel having therein a head positioning device to open an air flow passage in a subject, a pump having an air hose running to a face mask, said mask being secured by said head positioning device for a sealed engagement of said mask with the nose and mouth of the subject, an oxygen line running from an oxygen cylinder to communicate with said air hose to said mask, a valve carried by said mask providing communication between said air hose and said mask, said valve permitting in the alternative oxygen enriched air under pump pressure to the subject or ambient air under atmospheric pressure to be breathed by the subject and a relief valve carried by said mask indicating the passage of oxygen enriched air under pump pressure to the subject and relieving excessive pressure with respect to said oxygen enriched air being supplied to the subject.

The above and like objects and advantages of the invention will be set forth in the following description made in connection with the accompanying drawing in which like reference characters refer to similar parts through the several views thereof.

BRIEF DESCRIPTION OF THE DRAWINGS

FIG. 3 is a composite view showing the invention herein substantially as indicated in FIG. 1 in perspective and a portion thereof being shown in a broken top plan view in operating position; and FIG. 4 is a broken view in perspective showing a portion of the invention herein.

DESCRIPTION OF A PREFERRED EMBODIMENT

Figure 1:
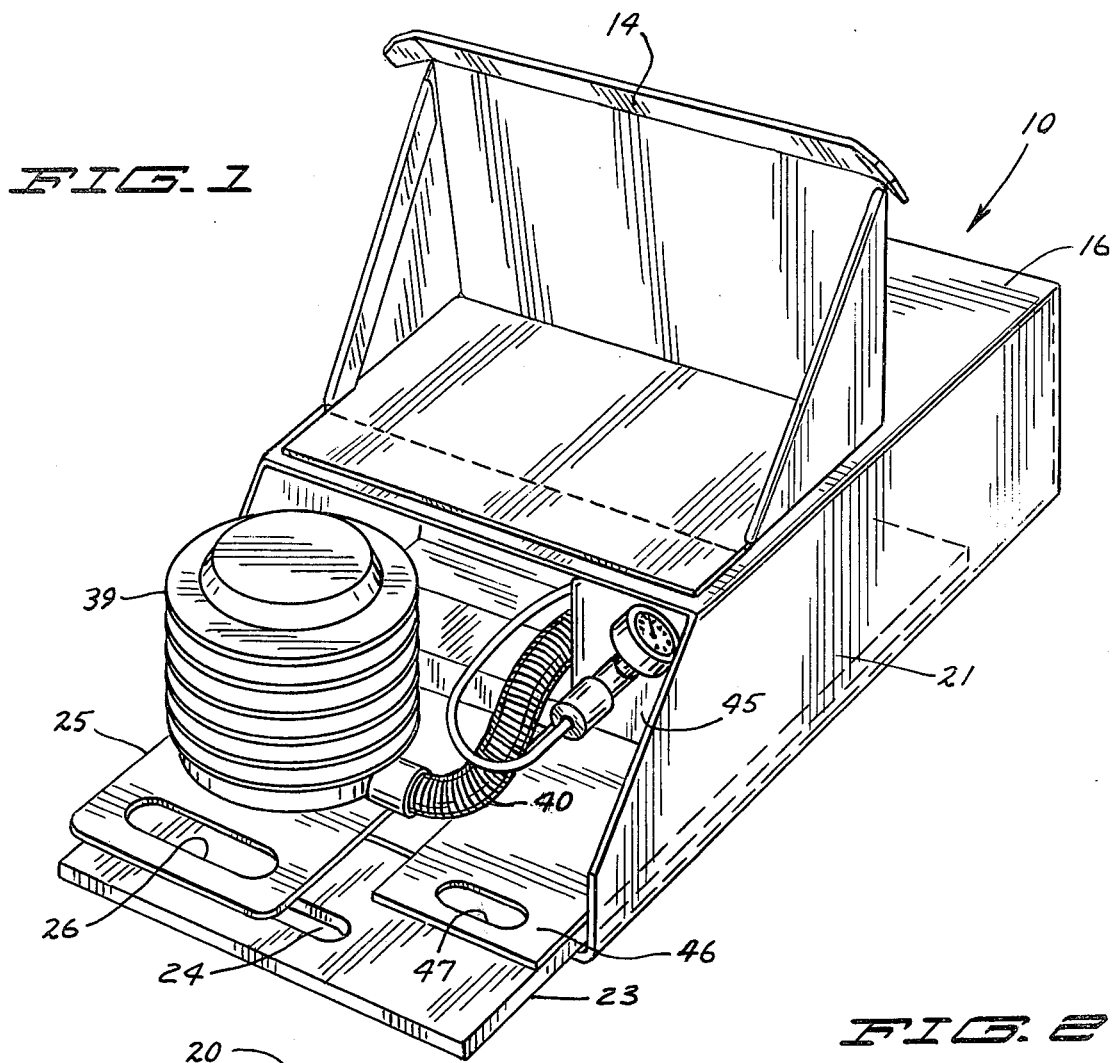
FIG. 1 is a view in perspective showing the invention herein.
Figure 2:
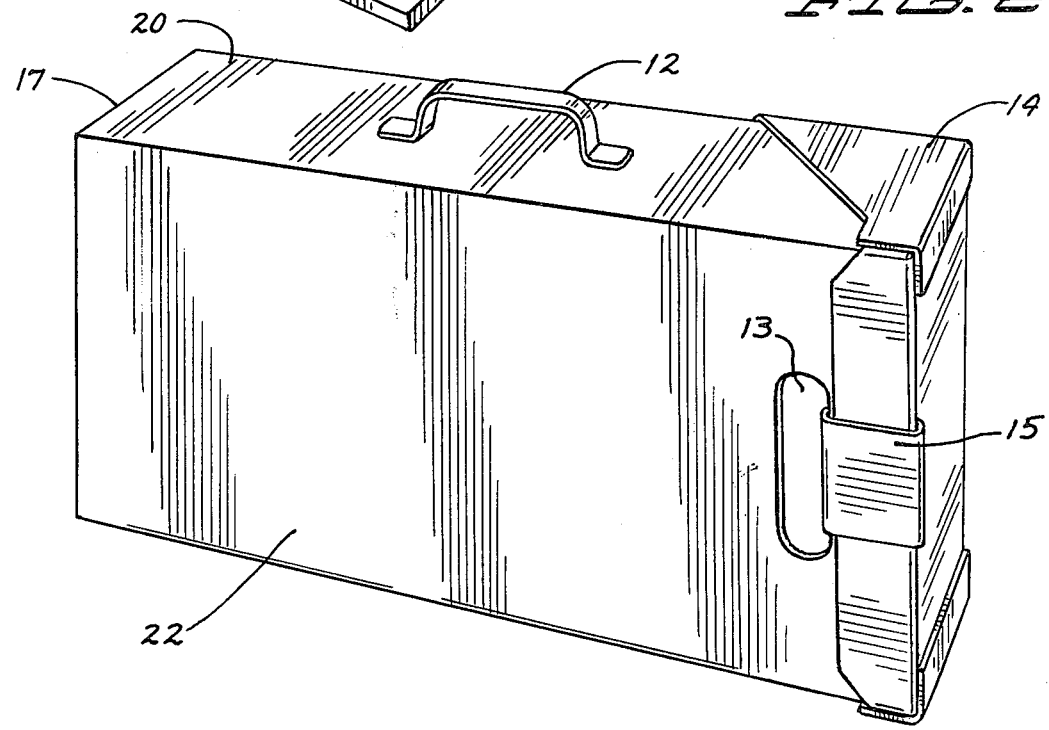
FIG. 2 is a view in perspective showing the container of the invention herein in closed position.

Referring to the drawings, the apparatus herein is made up of a container or carrier 10 shown comprising a suitable carrying case substantially parallepiped in form having a handle 12, a hinged end lid 14 shown here being carried by the top wall 16, said lid carrying a latch member 15 having a lip portion extending through a cut out hand hold 13 as indicated in FIG. 2, and the same being a conventional type of friction clasp. Said container further comprises an end wall 17, side walls 20 and 21 and a bottom wall 22. Said container is shown in its present form for purposes of illustration and not for purpose of limitation as to its design.

Said container has disposed therein in operative relationship the elements in combination which as will be described provide an apparatus which embodies the elements necessary to the effort towards respiratory restoration and cardiac resuscitation.

Disposed overlying the bottom wall of said container 10 is a panel member 23 having a cut out handle 24 and the same forms a rigid spine board in connection with cardiac chest compression as will be described.

Disposed within said container overlying said spine board 23 is a panel member 25 having a cut out handle 26 adjacent the open end of said container. Said panel member is here shown as being a substantially flat plate member approximately one half the width of said container and slidable out of said container adjacent the hinged end thereof. Mounted on said panel is a head positioning device 28 consisting of a substantially triangular upstanding neck rest member 29 which has substantial firmness and is of such height that when positioned under the neck of a subject that it will tilt the head of the subject rearwardly and downwardly to angle the chin almost directly upwardly whereby the airway or air passage through the throat of the subject will be opened up. The word subject as used herein refers to a person requiring respiratory restoration and/or cardiac resuscitation as indicated by 5 in FIG. 3. Carried by said head positioning device are straps 34 and 35 at each end thereof and a strap 36 which enters rearwardly thereof and the same will be further described.

Also carried on said panel is a conventional type of air pump 39 formed as of suitable polyvinyl chloride, the same being shown here of a coiled or convoluted form which will be sufficiently resilient to be self restoring as to its upstanding operating position and the same may have disposed therein a upstanding position restoring spring which is not here shown. Said pump will have a suitable one-way valve embodied therein of conventional structure which is not here shown and automatically closing on the pumping or compression stroke and opening for the entrance of air on the upward or return stroke of said pump.

Said pump will draw ambient air therein in a conventional manner when the same returns from a compressed position to an upstanding extended position. In a compression stroke said pump will be designed to have a capacity to deliver 500–600 cc of air per stroke.

Extending from said pump is a flexible air hose 40 which is suitably sized and is here indicated as being on the order of three quarters of an inch I.D.

Also disposed within said container is an oxygen cylinder 45 providing a pressurized supply of oxygen and having a conventional control valve 44 thereon and said cylinder is carried on a panel 46 disposed alongside of said panel 25, the same having a cut out handle 47 for easy withdrawal outwardly of said container.

A hose 42 of a fairly small diameter such as on the order of $\frac{1}{8}$" I.D. runs from said oxygen cylinder to tap said hose 40 as by a conventional T-fitting 48 as shown in FIG. 3.

The air pumped through the air hose 40 will be mixed with oxygen passing through said hose 42 to provide oxygen enriched air, the mixture of which is readily controlled by operation of the valve member 44.

Carried at the free end of said air hose 40 is a valved face mask 50 which overlies the mouth and nose portion of the subject as shown in FIG. 3. Said mask is secured as shown by the straps 34, 35 and 36 taken with the buttons 55.

Extending through the nose portion 51 of said mask is a cylindrical valve member 54 opening into said mask and having the air hose 40 secured to a nipple portion 53 thereof.

An indicating relief valve member 56 is provided in connection with said valve member adapted to project outwardly to give a visual indication that pressurized oxygen enriched air is passing into the mask and responsive to the presence of excessive pressure such as in excess of 30 CM of water, said member 56 projects further sufficiently to open ports to the atmosphere to relieve pressure in excess of said amount. Said indicating relief valve member is designed to regulate the pressurized air to the subject to be at an acceptable level.

Said mask 50 is of a generally conventional design formed having a peripheral edge or perimeter adapted to snugly lie upon the face of the subject.

Carried on said panel is a self powered rhythm device 60 arranged to emit an audible signal to provide timing for external cardiac or chest compression emitting audible signals such as at the rate of 60 or 80 signals per minute for the restoration of a normal pulse rate. Said device is of conventional structure and has a switch 61 moveable to indicate 60 or 80 audible beat signals per minute as indicated in FIG. 3. In addition said device is shown having a visual light emitting or blinking signal 62 accompanying said audible signal. Said rhythm device has a spring loaded underlying "on" switch 60a of conventional design not shown which commences the operation of the rhythm device upon removal of the plate member 25 from said container 10.

Basic life support in emergency first aid treatment requires recognizing respiratory and cardiac arrest and starting immediately the necessary resuscitation procedures to maintain life.

The procedures should be commenced without delay under a maximum sense of urgency.

The necessary steps could be carried out by hand. However, the use of appropriate equipment as provided by the invention herein enhances greatly the effectiveness and efficiency of carrying out the procedures and the chance for survival of the subject.

The first regard is for respiration. The lid of the container is opened, the spine board 23 and the panel 25 are immediately removed and positioned as indicated in FIG. 3 with the subject being positioned thereon to have his head and neck placed over the head positioning member 29 whereby his head will be tilted back to bring his chin into an upward vertical position and the air passage of the subject will be opened. At the same time the valve 44 of the oxygen cylinder 45 is opened. The oxygen cylinder may be fully withdrawn from the container by merely pulling out its support board 46.

In an effort to restore respiration, the mask 50 is positioned immediately as indicated in FIG. 3, the same being in a sealed position over the chin, mouth and nose of the subject and secured by the straps 34, 35 and 36. The valve 54 permits free passage of ambient air to the subject for normal breathing. The subject will be given immediately the generally prescribed four strokes of oxygen-enriched air by four compressions of the pump 39. Frequently the air pumped into the subject is sufficient to commence respiration. Immediately after providing the four strokes of air, the operator should determine if the subject has a pulse. In the absence of a pulse, there can be assumed to be a cardiac arrest. With the panel 25 positioned as indicated in FIG. 3 and the operator kneeling at the side of the subject, the rhythm device will have been automatically activated, thus move the switch 61 to provide an audible beat at the rate of either 60 or 80 times per minute. The beat of 80 times per minute is desirable where one person is operating the entire device.

The operator will then commence cardiac or chest compression with the spine board giving firm underbody support. The chest compression will be in the rhythm of the timing device and after each fifteen compression strokes, there will be provided to the subject, as generally prescribed, two breaths of oxygen enriched air by two compressions of the pump 39 and this operation will be continued in this sequence until advanced life support assistance is present to treat the subject.

The valve structure 54 normally provides for the free passage of ambient air to the subject and when the pump 39 is compressed, the entry into the valve structure of oxygen enriched air under pump pressure seals off ambient air and ventilates the subject. When the pump is at rest, there is still some passage of oxygen under the oxygen tank pressure which passes slowly through a by-pass in the valve 54 and mixes with the ambient air so that the subject is always provided oxygen additional to what is present in the ambient air.

The pump is preferably of a size and capacity sufficient to provide 500–600 cc of air per compression stroke thereof. In the event that the oxygen enriched air pumped into the subject is at a relatively excessive pressure, a pressure relief valve 56 provides automatic relief.

The oxygen system herein is preferably regulated for a constant two liter per minute flow which would be 33 ccs per second put into the ventilation or air hose 40 at a point 18 inches from the mask whereby there will be an accumulation on the order of 150 cc of oxygen contained in the hose and mask in each interval between ventilation or compression strokes on the pump. In the event two persons operate the apparatus, there will be one ventilation stroke or compression stroke of the pump to pump oxygen-enriched air into the subject following each fifth chest compression with the chest compression to be on the order of one second per minute each. Thus with the timing device set for a rhythm count of 80 beats per minute for one operator of 60 beats per minute in the case of two operators, each, there will be on the average of 60 chest compression strokes per minute with respect to the subject.

With the accumulation of 150 cc of oxygen as above described, there will be a maximum pressure for lung inflation with the subsequent compression stroke of the pump which provides for putting the highest level of oxygen into the lungs of the subject.

Thus there is provided here an apparatus consisting of the elements in cooperative relationship to open the air passage of the subject and to insure an efficient and effective supply of oxygen enriched air with the apparatus being so positioned with respect to the subject that its continued operation is a convenient and effective one in connection with the attendant cardiac compressions essential to restore the heartbeat of the subject.

It will of course be understood that various changes may be made in form, details, arrangement and proportions of the parts without departing from the scope of the invention herein which, generally stated, consists in an apparatus capable of carrying out the objects above set forth, in the parts and combination of parts disclosed and defined in the appended claims.

What is claimed is:

1. A cardiac pulmonary resuscitation apparatus for use in connection with a person having a cardiac arrest, having in combination
   a container having end opening means,
   a panel slidably removable from said container through end opening means,
   a head positioning member carried on said panel, said member being upstanding such as to support the head of a person in prone position to tilt the head to open the air passage of said person,
   an air pump carried on said panel having an air hose extended therefrom,
   an oxygen cylinder carried in said container,
   an oxygen line running from said oxygen cylinder to said air hose,
   a face mask carried at the free end of said air hose having spaced holding means to be engaged by strap members,
   strap members carried by said head positioning member engaging said last mentioned holding means and securing thereto said face mask in operating position,
   a valve member integral with said face mask having said air hose secured thereto,
   said valve member passing ambient air through said face mask, and means carried by said valve member responsive to the passage of air through said air hose sealing off said passage of said ambient air.

2. The structure set forth in claim 1, including
   a rigid panel forming a spine board removably disposed into said container cooperating with said first mentioned panel to form an extension thereof to support a person in prone position requiring resuscitation.

* * * * *